United States Patent [19]
Barrett

[11] Patent Number: 5,837,694
[45] Date of Patent: Nov. 17, 1998

[54] METHOD FOR ENHANCING NEURONE SURVIVAL AND AGENTS USEFUL FOR SAME

[75] Inventor: Graham Leslie Barrett, Northcote, Australia

[73] Assignee: The Walter and Eliza Hall Institute of Medical Research

[21] Appl. No.: 633,792

[22] PCT Filed: Oct. 18, 1994

[86] PCT No.: PCT/AU94/00631

§ 371 Date: Jul. 1, 1996

§ 102(e) Date: Jul. 1, 1996

[87] PCT Pub. No.: WO95/11253

PCT Pub. Date: Apr. 27, 1995

[30] Foreign Application Priority Data

Oct. 18, 1993 [AU] Australia ................. PM 1870

[51] Int. Cl.$^6$ .......... A61K 48/00; C07H 71/04; C12Q 1/68; C12N 15/85
[52] U.S. Cl. ............ 514/44; 435/6; 435/91.1; 435/325; 435/366; 435/375; 536/23.1; 536/24.31; 536/24.5
[58] Field of Search ............. 514/44; 536/23.1, 536/24.5, 24.31; 435/6, 91.1, 375, 325, 366

[56] References Cited

U.S. PATENT DOCUMENTS 5,585,479 12/1996 Hoke et al. ................. 536/24.5

OTHER PUBLICATIONS

Westermann et al., Inhibition of expression of SV–40 virus large T–antigen by antisense oligodeoxyribonucleotides, Biomed. Biochim. Acta, vol. 48(1), pp. 85–93, 1989.

James, Towards gene inhibition therapy: a review of progress and prospects in the field of antiviral antisense nucleic acids and ribozymes, Antiviral Chemistry and Chemotherapy, vol. 2(4), pp. 191–214, 1991.

Uhlmann et al., Antisense oligonucleotides: a new therapeutic principle, Chemical Reviews, vol. 90(4), pp. 543–584, Jun. 1990.

Weiss, Upping the antisense ante, scientist bet on profits from reverse genetics, Science News, vol. 139, pp. 108–109, Feb. 1991.

Tseng et al., Antisense oligonucleotide technology in the development of cancer therapeutics, Cancer Gene Therapy, vol. 1(1), pp. 65–71, Mar. 1994.

Gewirtz et al., Facility oligonucleotide delivery: helping antisense deliver on its promise, Proc. Natl. Acad. Sci., vol. 93, pp. 3161–3163, Apr. 1996.

Barrett et al., The p75 nerve growth factor receptor mediates survival of death depending on the stage of sensory neuron development, Proc. Natl. Acad. Sci., vol. 91, pp. 6501–6505, Jul. 1994.

Chao, M.V. et al. (1986) "Gene Transfer and Molecular Cloning of the Human NGF Receptor", *Science* 232:518–521.

Ross, Alonzo H. et al. (1991) "Nerve Growth Factor—Induced Differentiation of Human Neuroblastoma Cell Lines" *Chem. Abstracts*115:229, Abstract No. 151785d.

Wagner, R.W. (1994) "Gene Inhibition Using Antisense Oligodeoxynucleotides " *Nature*(372):333–335.

International Patent Application PCT/US93/08446 (Int. Publication No. Wo 94/06935).

*Primary Examiner*—John L. LeGuyander
*Assistant Examiner*—Andrew Wang
*Attorney, Agent, or Firm*—Scully, Scott, Murphy & Presser

[57] ABSTRACT

Antisense oligonucleotides to nerve growth factor receptor, p75$^{NGFR}$ gene downregulate expression, thereby facilitating neurone survival.

14 Claims, 14 Drawing Sheets

Age at Lesion: 3 days
Treatment: 5 days
Method of treatment: 50uM Antisense in 20% pluronic gel soaked gelfoam applied to cut proximal end of sciatic nerve.

METHOD FOR ENHANCING NEURONE SURVIVAL AND AGENTS USEFUL FOR SAME

This application is a 371 of PCT/AU94/00631, filed Oct. 18, 1994.

The present invention relates generally to neurones and more particularly to a method for increasing or enhancing survival of same. The present invention further contemplates agents in the form of compositions of matter useful for facilitating survival of neurones.

Bibliographic details of the publications numerically referred to in this specification are collected at the end of the description. Sequence Identity Numbers (SEQ ID NOs.) for the nucleotide sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

A number of soluble trophic factors have been shown to exhibit an effect on neuronal survival in vivo. Many of these factors act directly on the developing neurone within, for example, the dorsal root ganglia (DRG). One factor of particular importance is Nerve Growth Factor (NGF; 1). The effects of NGF are mediated at least in part by trkA, the high affinity NGF receptor. Another receptor, the low affinity NGF receptor $p75^{NGFR}$, is a receptor, the function of which, is incompletely characterised. The $p75^{NGFR}$ receptor has been shown to increase affinity of trkA for NGF (12) and work by Lee et al (2) suggests that $p75^{NGFR}$, is required for development of sensory neurones. Notwithstanding that administration of NGF may have therapeutic potential in facilitating survival of neurones, NGF is a multifunctional molecule affecting a range of target cells. There is a need, therefore, to specifically target neuronal cells.

In work leading up to the present invention, the inventors sought to further characterise the function of $p75^{NGFR}$ by down regulating the receptor in sensory neurones from DRG at various stages of development. The inventors surprisingly discovered that lowering levels of $p75^{NGFR}$, expression in sensory neurones increases the survival of postnatal (P) day 2 (P2) sensory neurones in the absence of exogenous NGF notwithstanding that the down regulation of $p75^{NGFR}$ expression prevents NGF-mediated survival of sensory neurons at the embryonic (E) stage of target innervation.

Accordingly, one aspect of the present invention contemplates a method of facilitating neuronal survival in an animal, said method comprising down regulating expression of a receptor on said neurones for a neurotrophic factor capable of neurotrophic factor-mediated survival of neurones.

The present invention is exemplified and described herein with reference to the receptor, $p75^{NGFR}$ and to one of its effector molecules, i.e. NGF. This is done, however, with the understanding that the present invention extends to all neurotrophic receptors which act in a manner functionally analogous to $p75^{NGFR}$ and its effector molecules which include NGF and Brain Derived Neurotrophic Factor (BDNF) in promoting neurone survival as determined in accordance with the present invention. Neurones contemplated by the present invention are those which express or have the ability to express $p75^{NGFR}$. By "facilitating neuronal survival" is meant to include increasing or enhancing survival of neurones or rescuing neurones following, during or prior to neurodegenerative conditions such as associated with disease and/or trauma. "Rescuing neurones" includes maintenance of the differentiated state of a neurone such as, for example, maintaining the cholinergic differentiated state of a neurone. In this regard, therefore, a related aspect of the present invention provides a method of facilitating neuronal rescue in an animal, said method comprising down regulating expression of a receptor on said neurones for a neurotrophic factor capable of neurotrophic factor-mediated rescue of neurones.

Accordingly, in a preferred aspect of the present invention, there is provided a method of facilitating survival of neurones which express receptor $p75^{NGFR}$ in an animal, said method comprising down regulating $p75^{NGFR}$ expression in said neurones.

Neurones which express or have the ability to express $p75^{NGFR}$ and which are encompassed by the present invention include, but are not limited to, sensory neurones, sympathetic neurones, central cholinergic neurones (and in particular basal forebrain neurones which are affected in Alzheimer's disease), motor neurones and cerebellar neurones and neurones at the substantia nigia and stinatum, involved in Parkinson's Disease.

Preferably, the animal is a mammal such as a human, livestock animal (e.g. sheep, pig, cow, horse or goat), companion animal (e.g. dog or cat), laboratory test animal (e.g. mouse, rat, rabbit or guinea pig) or captive wild animal. Most preferably, the animal is a human.

The term "down regulating" is used in its most general sense and includes decreasing the number of receptors per cell, decreasing the number of functional receptors per cell and/or blocking existing receptors on a cell. In each case, the down regulated expression results in increased survival of sensory neurones. Analysis of $p75^{NGFR}$ receptor expression may be monitored by any convenient means such as, but not limited to, use of labelled antibodies and/or through analysis of gene expression.

Preferably, the facilitation of neuronal survival is at the stage of or after target innervation.

In its most preferred embodiment, down regulation is at the genetic level through use of antisense nucleic acid molecules. In a particular exemplified embodiment, the antisense nucleic acid molecules are antisense oligonucleotides. Generally, short oligonucleotides are used having from about 5 to about 50 nucleotides depending on their target. Preferably, the oligonucleotides are from about 10 to less than about 26 nucleotides in length. Preferably, the antisense oligonucleotides target the 5' end portion of the $p75^{NGFR}$ gene or a region comprising and/or adjacent to the termination codon on the $p75^{NGFR}$ gene.

The present invention extends, however, to larger nucleic acid molecules capable of targeting mRNA of the structural $p75^{NGFR}$ genetic sequence or a gene regulating $p75^{NGFR}$ expression.

A related embodiment is directed to a method of down regulating expression of the low affinity nerve growth factor (NGF) receptor, $p75^{NGFR}$ on a neurone, said method comprising contacting said neurone with an effective amount of an antisense oligonucleotide to the gene encoding $p75^{NGFR}$ for a time and under conditions sufficient to reduce expression of $p75^{NGFR}$ such that neurone survival is facilitated.

More particularly, there is provided a method of down regulating expression of the low affinity nerve growth factor (NGF) receptor, $p75^{NGFR}$ on a neurone, said method comprising contacting said neurone with an effective amount of an antisense oligonucleotide to the gene encoding $p75^{NGFR}$ for a time and under conditions sufficient to reduce expression of p75$^{NGFR}$ such that in the absence of exogenously added NGF, neurone survival is increased, enhanced or otherwise facilitated.

The oligonucleotides are preferably chemically modified to facilitate improved or increased stability in vitro and/or in vivo (e.g. against the action of nucleases) and/or to allow oral bioavailability, to permit transfer across the blood-brain barrier and/or to increase the therapeutic index. Furthermore, the chemical modification may facilitate administration into the target animal or, following administration, passage of the oligonucleotides to the target tissue. For example, the oligonucleotides may carry linkers, tags or other effector molecules such as transferrin receptor antibody. Particularly preferred oligonucleotides are phosphorothioate oligonucleotides since phosphorothioates exhibit resistance to nucleases contributing to high stability both in vitro and in vivo (3). Alternatively, the oligonucleotides may be conjugated to lipophilic groups (13), conjugated to meso-tetracarboxyporphine (14), conjugated to poly-L-lysine (15) or conjugated to protein via poly-L-lysine (16). The oligonucleotides of the present invention may be administered to the target animal by any suitable means including through the intravenous, intramuscular, intranasal, rectal, intraperitoneal, intracerebral, intrathecal or subcutaneous routes; also via liposomes or retrograde transport; or locally to sites of peripheral nerve damage or injury such as using a slow release composition such as Gel-foam. As the oligonucleotides exhibit little if any toxicity to a target animal, they may be administered in any appropriate concentration provided that sufficient antisense molecules reach the target site. Appropriate ranges of concentration include, for in vivo use from about 0.01 $\mu$M to >2,000 $\mu$M, more preferably from about 0.05 $\mu$M to about 1,500 $\mu$M and even more preferably from about 0.1 $\mu$M to about 1,000 $\mu$M. For topical use, subcutaneous use or local use, similar concentrations may be used although higher concentrations would not be deleterious to the treatment of the condition.

According to another aspect of the present invention there is provided an oligonucleotide capable of down regulating expression of the p75$^{NGFR}$ in neurones. More particularly, the oligonucleotide of the present invention is capable of down regulating expression of p75$^{NGFR}$ in neurones such that after the stage of target innervation, there is increased, enhanced or otherwise facilitated survival of neurones.

The oligonucleotides of the present invention may be selected for targeting almost any part of p75$^{NGFR}$ mRNA, with the preferred oligonucleotide and length of oligonucleotide resulting in a decrease of at least 30%, more preferably at least 50% and even more preferably at least 60% or more in the level of expression of p75$^{NGFR}$ in neurones.

The preferred oligonucleotides are 5'-ACCTGCCCTCCTCATTGCA-3' (SEQ ID NO:1) which targets the 5' end portion of the p75$^{NGFR}$ gene (also referred to herein as "5'-AS") and 5'-AGTGGACTCGCGCATAG-3' (SEQ ID NO:4) which targets the region comprising and/or adjacent to the termination codon of the p75$^{NGFR}$ gene (also referred to herein as "3'-AS"), including any or all mutants, derivatives, homologues or analogues thereof which are capable of hybridising or forming a duplex with at least part of p75$^{NGFR}$ mRNA. Conveniently, the preferred oligonucleotide is a phosphorothioate oligonucleotide or is otherwise chemically modified as contemplated above.

Accordingly, another aspect of the present invention provides an oligonucleotide:

(i) which is capable of down regulating expression of p75$^{NGFR}$ in neurones; and (ii) which is capable of hybridising under low stringency conditions to the reverse complement of SEQ ID NO:1; or (iii) which is capable of hybridising under low stringency conditions to the reverse complement of SEQ ID NO:4.

For the purposes of defining the level of stringency, reference can conveniently be made to Maniatis et al (17) at pages 387–389 which is herein incorporated by reference where the washing steps disclosed are considered high stringency. A low stringency is defined herein as being in 4–6×SSC/0.1–0.5% w/v SDS at 37°–45° C. for 2–3 hours. Depending on the source and concentration of nucleic acid involved in the hybridisation, alternative conditions of stringency may be employed such as medium stringent conditions which are considered herein to be 1–4×SSC/0.25–0.5% w/v SDS at $\geq$45° C. for 2–3 hours or high stringent conditions considered herein to be 0.1–1×SSC/0.1% w/v SDS at $\geq$60° C. for 1–3 hours.

According to a preferred aspect of the present invention, there is contemplated a method of increasing, enhancing or otherwise facilitating survival of neurones which express p75$^{NGFR}$ said method comprising contacting neurones with an effective amount of an oligonucleotide which is substantially antisense to at least part of p75$^{NGFR}$ mRNA under conditions sufficient for said oligonucleotide to penetrate said neurones and down regulate expression of p75$^{NGFR}$. Upon down regulation of p75$^{NGFR}$ expression, the survival of neurones is increased, enhanced or otherwise facilitated. This is especially evident in the absence of exogenously supplied NGF. Preferably, the survival of neurones is at or after the stage of target innervation.

In a related embodiment, the present invention contemplates a method of delaying further onset of a neurodegenerative condition associated with disease and/or trauma in a mammal, said method comprising administering to said mammal an effective amount of an antisense oligonucleotide capable of down regulating expression of p75$^{NGFR}$ on neurones.

In a further related embodiment, the present invention provides a method for the prophylaxis and/or treatment of neurodegenerative conditions associated with disease and/or trauma in a mammal, said method comprising administering to said mammal an effective amount of an antisense oligonucleotide for a time and under conditions sufficient to down regulate expression of p75$^{NGFR}$ on neurones. The downregulation of the p75$^{NGFR}$ receptor on neurones promotes rescue of neurones following onset of a neurodegenerative condition, disease or trauma. A neurodegenerative condition includes loss of phenotype, for example loss of cholinergic phenotype, associated with a neurone becoming undifferentiated. This is generally considered a stage prior to cell death. Accordingly, the present invention is directed to the treatment of neurodegenerative conditions characterised by reducing, preventing or rescuing neurones from loss of phenotype and/or cell death.

The oligonucleotides of the present invention may be "homologous" in that they are designed from the p75$^{NGFR}$ receptor mRNA sequence of the animal to be targeted or may be "heterologous" where the oligonucleotide is based on one species and cross-hybridises to the mRNA of another species. For example, where the genetic sequence encoding p75$^{NGFR}$ is similar in two species of animal, then an oligonucleotide based on one species may cross-hybridise to an extent sufficient to down regulate expression of the p75$^{NGFR}$ in the other species.

The present invention provides a method for the treatment and/or prophylaxis of animals with damaged neurones, or with potential for the further damage of neurones, which neurones are those which express $p75^{NGFR}$. The damage or potential damage may be from trauma or disease. The present invention, therefore, contemplates a method of treating conditions such as cerebral palsy, trauma induced paralysis, vascular ischaemia associated with stroke, neuronal tumours, motorneurone disease, Parkinson's disease, Huntington's disease, Alzheimer's disease, multiple sclerosis and peripheral neuropathies associated with diabetes, heavy metal or alcohol toxicity, renal failure and/or infectious diseases such as herpes, rubella, measles, chicken pox, HIV and/or HTLV-1.

According to this aspect of the present invention there is provided a method of treatment in an animal such as a human or other mammal, said method comprising down regulating expression of $p75^{NGFR}$ by, for example, one or more oligonucleotides which are antisense to at least part of $p75^{NGFR}$ mRNA or a functionally similar or analogous receptor in sensory neurones, preferably but not exclusively at or after the stage of target innervation.

In accordance with this aspect of the present invention, an agent capable of down regulating expression of $p75^{NGFR}$ is administered to the animal in an amount effective to down regulate expression of the receptor. Generally and preferably the agent is an antisense oligonucleotide designed to hybridise or form a duplex with at least part of $p75^{NGFR}$ mRNA thereby resulting in reduced $p75^{NGFR}$ expression.

Administration of the agent such as in the form of oligonucleotides may be by any convenient route, for example, by intravenous or intracerebral administration or by topical administration during or following surgical procedure. It may be necessary to treat the agent so as to reduce the action of host animal enzymes. For example, where the agent comprises an oligonucleotide, then the oligonucleotide is conveniently phosphorothioated. Alternative forms of administration include gene therapy and/or by use of viral vectors such as HSV vectors.

The present invention is predicated in part on the surprising discovery that in sensory neurones $p75^{NGFR}$ is able to mediate an apoptotic signal after the stage of target innervation but prior to target innervation is required along with trkA for NGF mediated survival of sensory neurones. Although not wishing to limit the present invention to any one theory or mode of action, it appears that the switch in function of $p75^{NGFR}$ at this late stage of cell development coincides with a decrease in levels of trkA expression in sensory ganglia, indicating that $p75^{NGFR}$ combines with trkA to mediate neuronal survival in the presence of NGF but, if not associated with trkA, $p75^{NGFR}$ may act as a death signal in the absence of an effective amount of in vivo NGF. Neurone survival may, therefore, be increased, enhanced or otherwise facilitated by one or more of down regulating expression of $p75^{NGFR}$, up regulating expression of trkA and/or supplying exogenous NGF or other suitable neurotrophic factors.

Accordingly, a further aspect of the present invention contemplates up regulating trkA expression to thereby modulate its interaction with $p75^{NGFR}$. Generally, according to this aspect of the present invention, trkA expression is up regulated using genetic means or through use of agonists. This and other aspects of the present invention may further comprise the addition of exogenous NGF or other suitable neurotrophic factors such as BNDF.

The term "up regulating" is used in its most general sense and includes increasing the number of receptors per cell, increasing the number of functional receptors per cell and/or enhancing the activity of existing receptors per cell.

The effects of the present invention in increasing, enhancing or otherwise facilitating survival of neurones after the stage of target innervation may be readily shown in vitro or in vivo. A particularly convenient in vivo model involves sciatic nerve axotomy in rats. In this procedure, the left sciatic nerve in new born rats is axotomised and the proximal stump of the sciatic nerve treated with antisense oligonucleotides or other agents capable of down regulating $p75^{NGFR}$ expression.

In a further embodiment of the present invention the $p75^{NGFR}$ may be used in an assay for $p75^{NGFR}$ binding molecules and preferably small binding molecules to be used as agonists or antagonists of cytokine-receptor binding. Preferably, cells expressing recombinant $p75^{NGFR}$ are used as the basis of the assay.

Still a further embodiment of the present invention contemplates the use of an oligonucleotide capable of down regulating expression of $p75^{NGFR}$ in neurones in the manufacture of a medicament for the treatment of a mammal with damaged neurones.

The present invention is further described by reference to the following non-limiting Figures and/or Examples.

Figure 3:
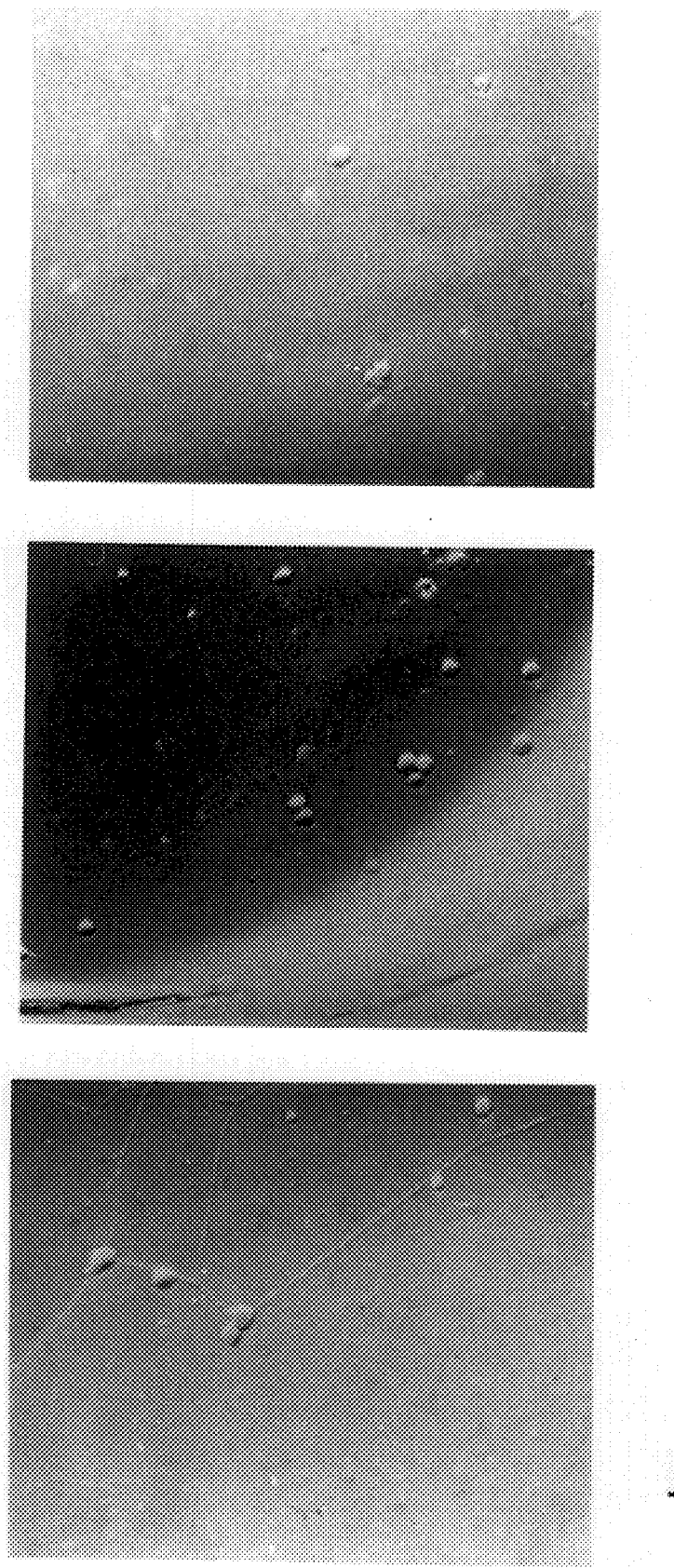

FIG. 3 is a photographic representation of phase-contrast micrographs of P2 mouse cells after 2 days in culture in the absence of NGF in the presence of 5 μm sense oligonucleotide (top), 1 μg/ml cycloheximide (middle) and 5 μm antisense oligonucleotide (bottom). Sense-treated cells exhibit various stages of apoptosis including shrinkage, crenation, cytoplasmic granularity and condensation, and membrane disruption. Increased survival occurred in both cycloheximide and antisense cultures. Due to inhibition of protein synthesis, cycloheximide-treated cells failed to develop neurites despite remaining phasebright and healthy in appearance. Anti-sense cultures show a large proportion of healthy cells with abundant neurites.

Figure 4A:
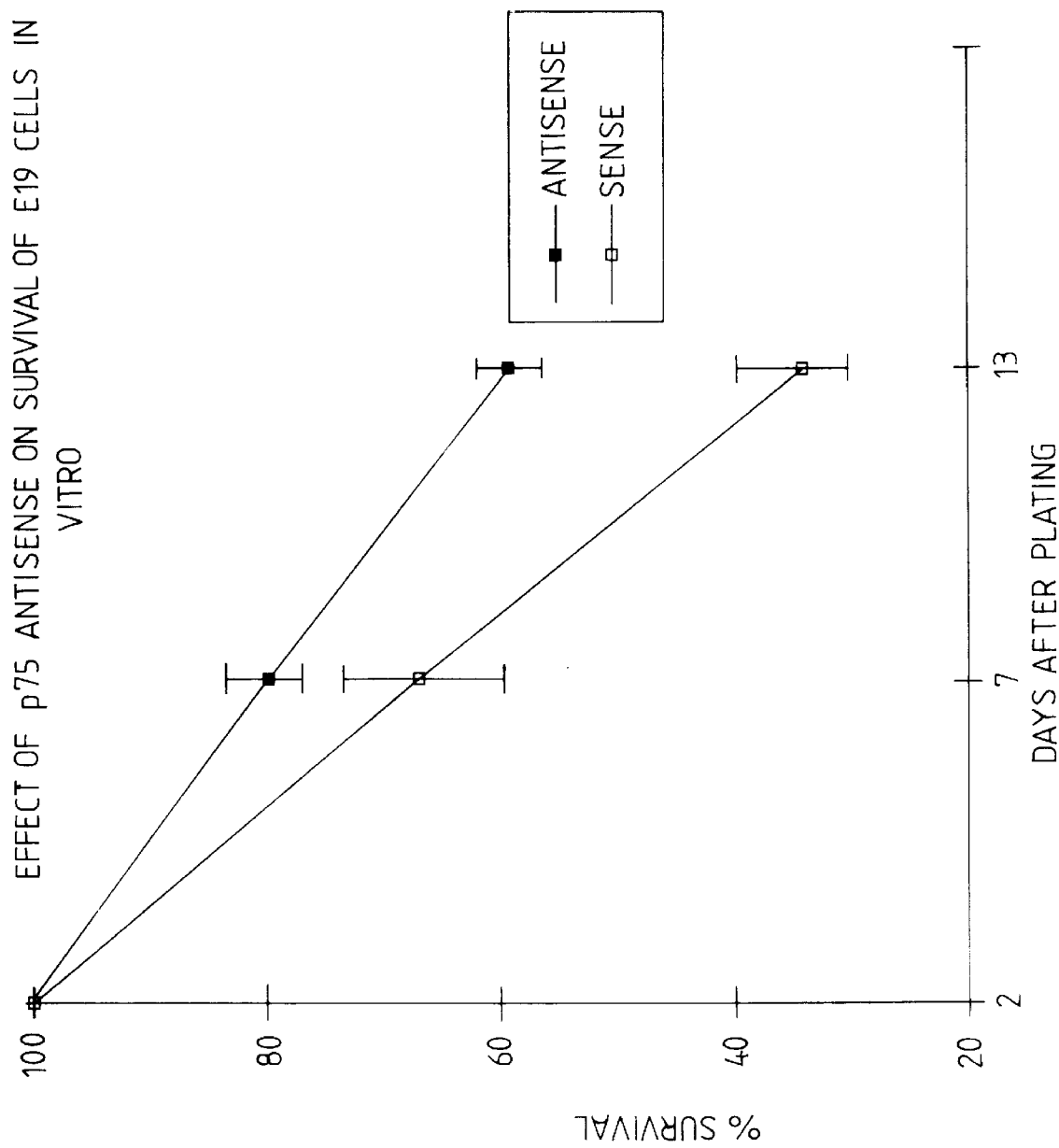

FIG. 4A is a graphical representation showing the effect of antisense and sense oligonucleotides on prolonged culture of DRG neurones from E19 mice. Oligonucleotides were added at the time of plating as was NGF at 1 μg/ml in order to keep the cells alive initially (this was unnecessary for P2 cells). There was no difference in survival of cells during the first two days, but after prolonged culture, increased survival in the antisense treated group became apparent. Values at each point are means±SEM (n=6).

Figure 4B:

FIG. 4B is a graphical representation of analysis by reverse transcriptase (RT)PCR of developmental modulation of trkA expression in mouse DRG. trkA mRNA was present at E15 and E19 but undetectable at P2. Freshly dissected DRG were snap frozen in liquid nitrogen and stored at −70° C. prior to homogenisation in 4M guanidinium thiocyanate and ultracentrifugation over a cesium chloride cushion.

RNA (100 ng) from each sample was incubated for one hour at 42° C. with AMV Reverse Transcriptase, and one fifth of the reaction products used for PCR (30 cycles, 1 min steps of 94° C., 55° C. and 72° C. in 100 μl with 2.5 units Taq polymerase (Cetus, USA)). Primers were:

TAGGCGGTCTGGTGACTTCGTTG (5')     (SEQ ID NO. 2)

and

ACATAGAGCTCCGTCAGGTTCCC (3')     (SEQ ID NO. 3)

with a predicted amplification product of 163 bp (based on the rat trkA sequence [6]).

Figure 5:
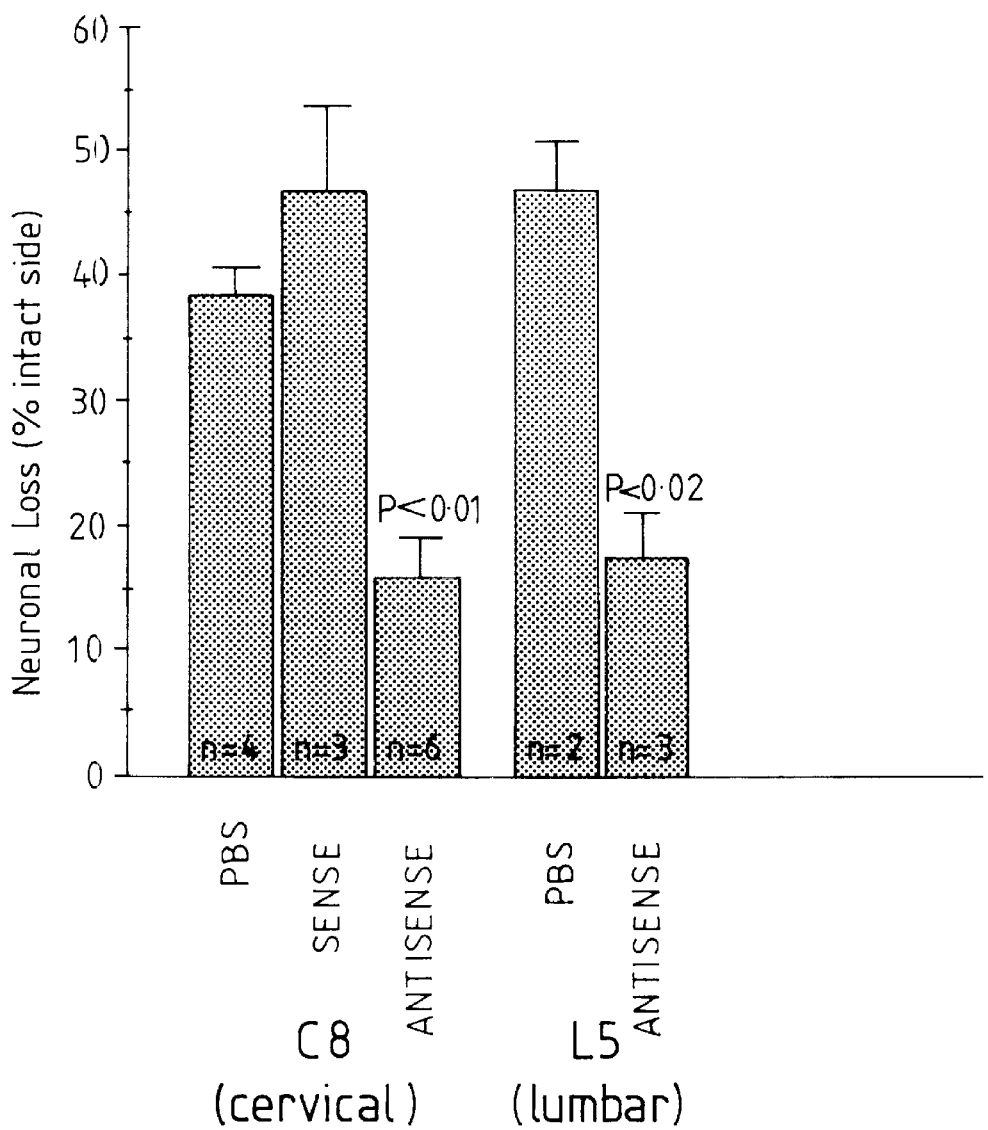

FIG. 5 is a graphical representation showing prevention of death of injured sensory neurones in vivo by $p75^{NGFR}$ receptor antisense oligonucleotides. C8, cervical; L5, lumba.

Figure 6:
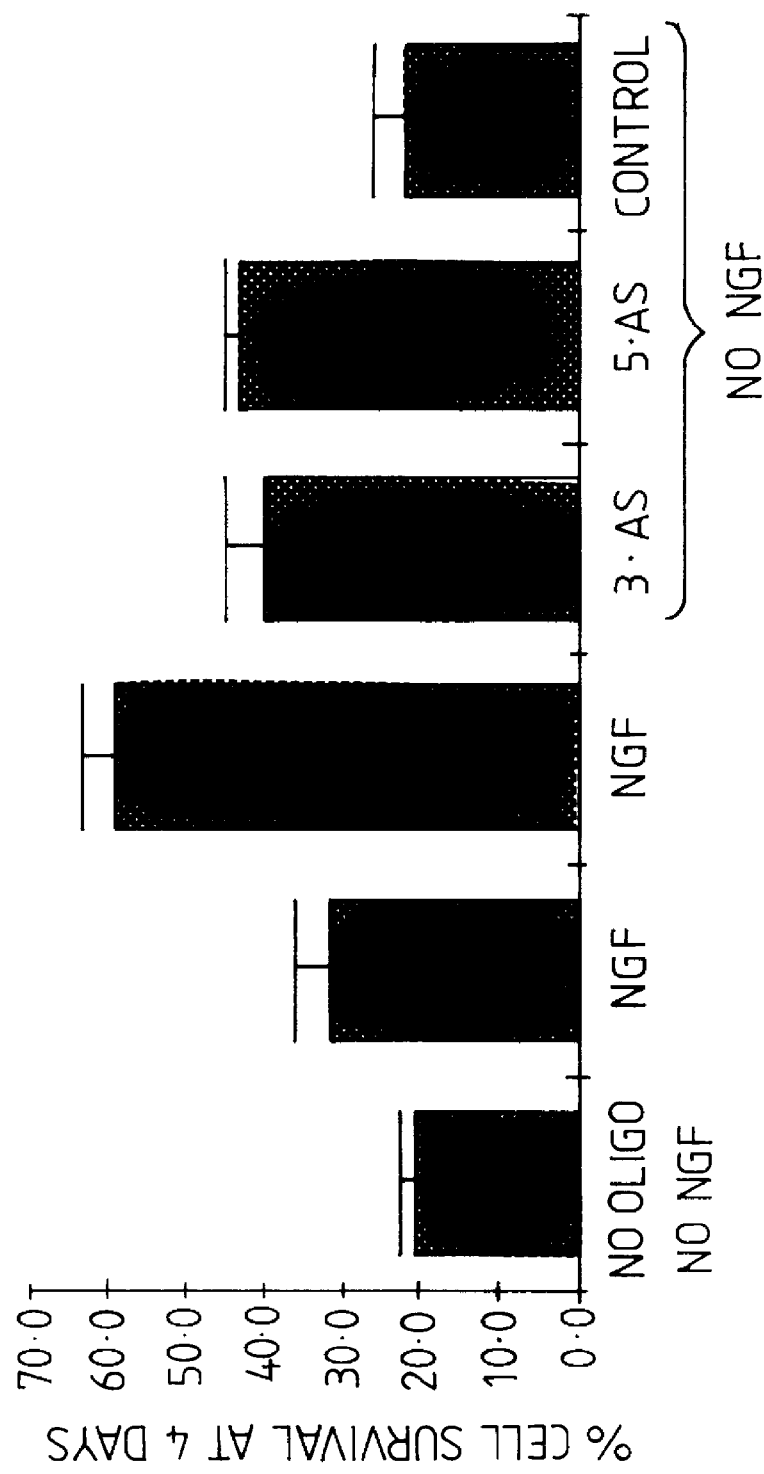

FIG. 6 is a graphical representation showing a DRG neuronal cell survival response in vitro using two $p75^{NGFR}$ antisense oligonucleotides. By way of comparison, controls include a non-oligonucleotide and a non-sense oligonucleotide (scrambled antisense oligonucleotide).

Figure 7:
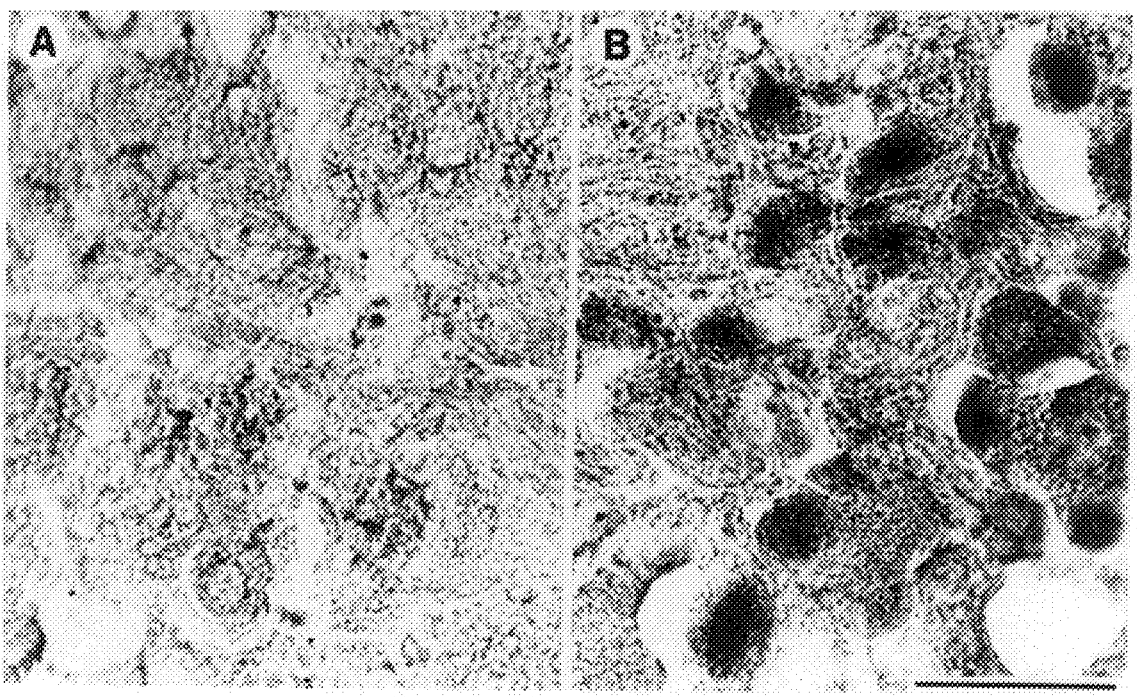

FIG. 7 is a photographic representation of sections of ipsilateral (B) and contralateral dorsal root ganglia (A) which have been stained with avidinperoxidase to detect the presence of biotinylated oligonucleotides after injection of these into one sciatic nerve.

Figure 8A:
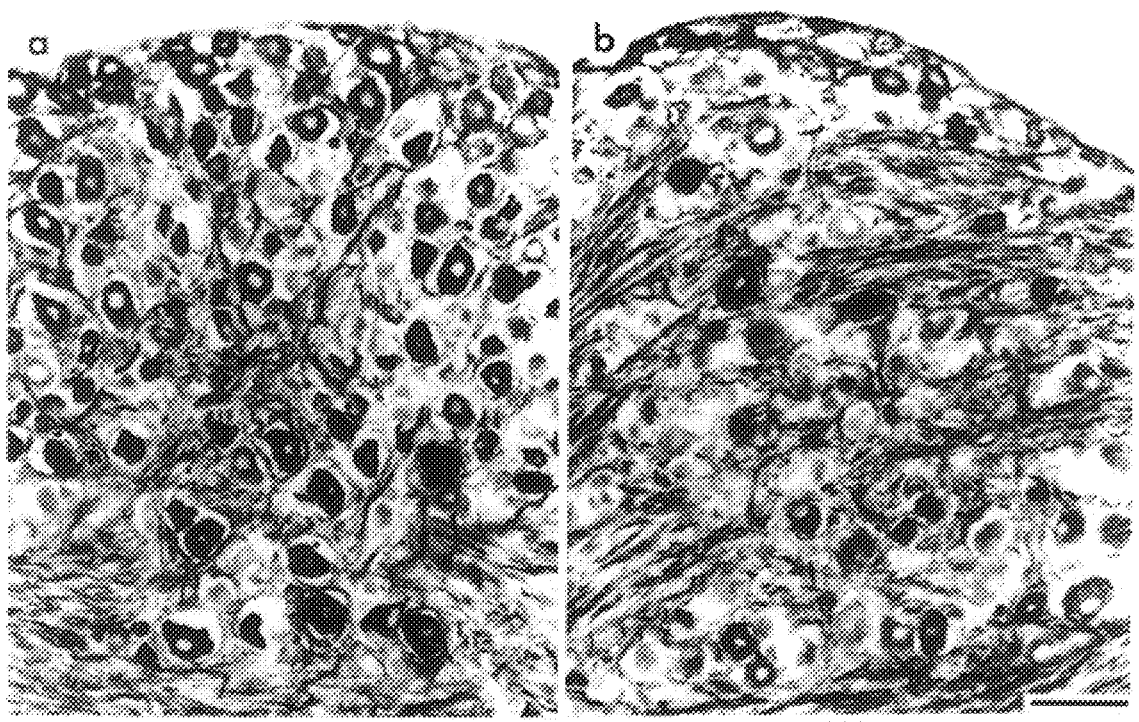

FIG. 8A is a photographic representation of sections of do which have been stained immunohistochemically for the presence of $p75^{NGFR}$. The sections were taken from intact (non-axotomized) dorsal root ganglia (on left) and from dorsal root ganglia of rats following axotomy and in vivo $p75^{NGFR}$ antisense treatment (on right).

Figure 8B:
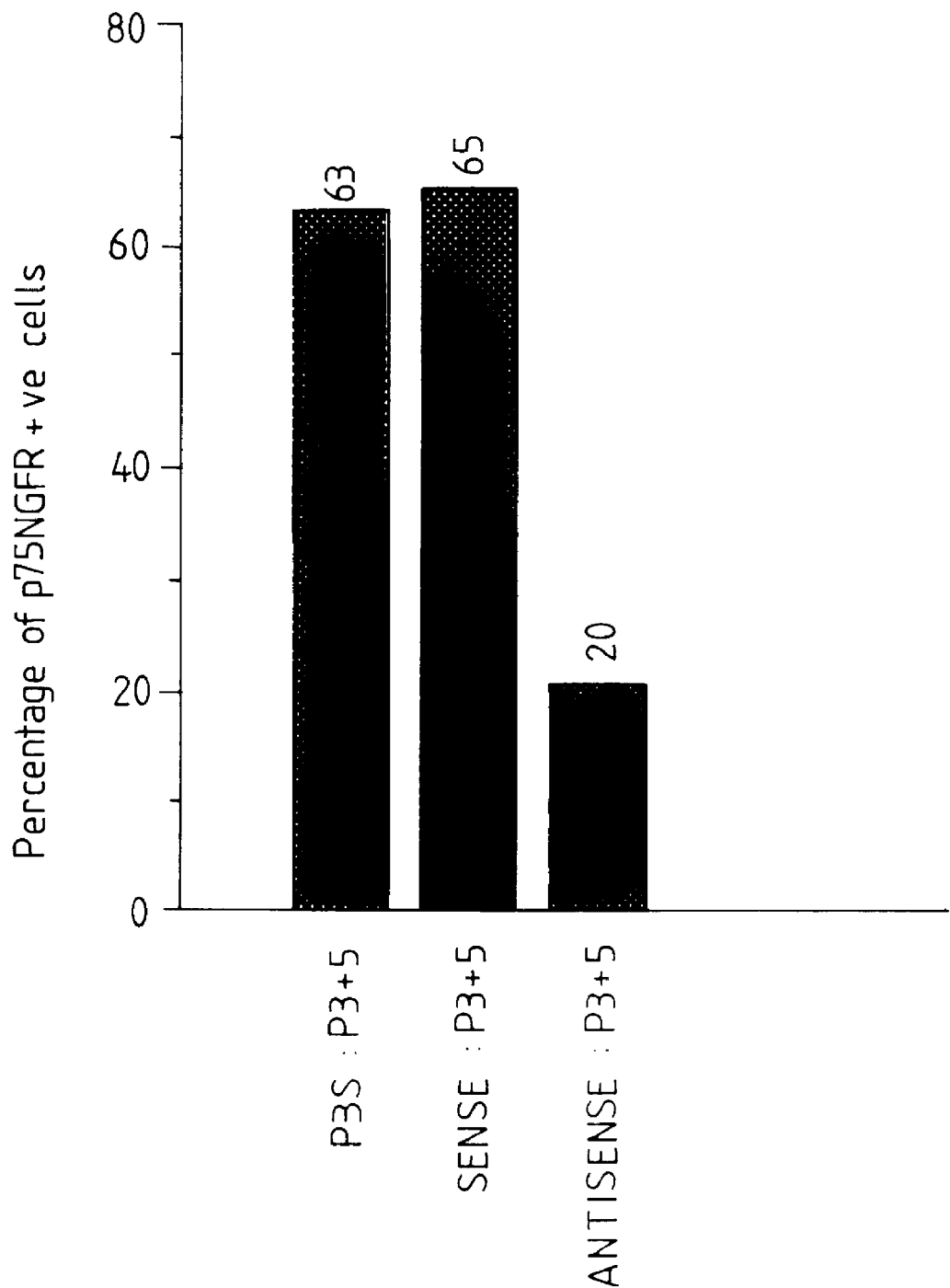

FIG. 8B is a graphical representation of $p75^{NGFR}$ down-regulation in vivo following antisense treatment compared to controls.

Figure 9:
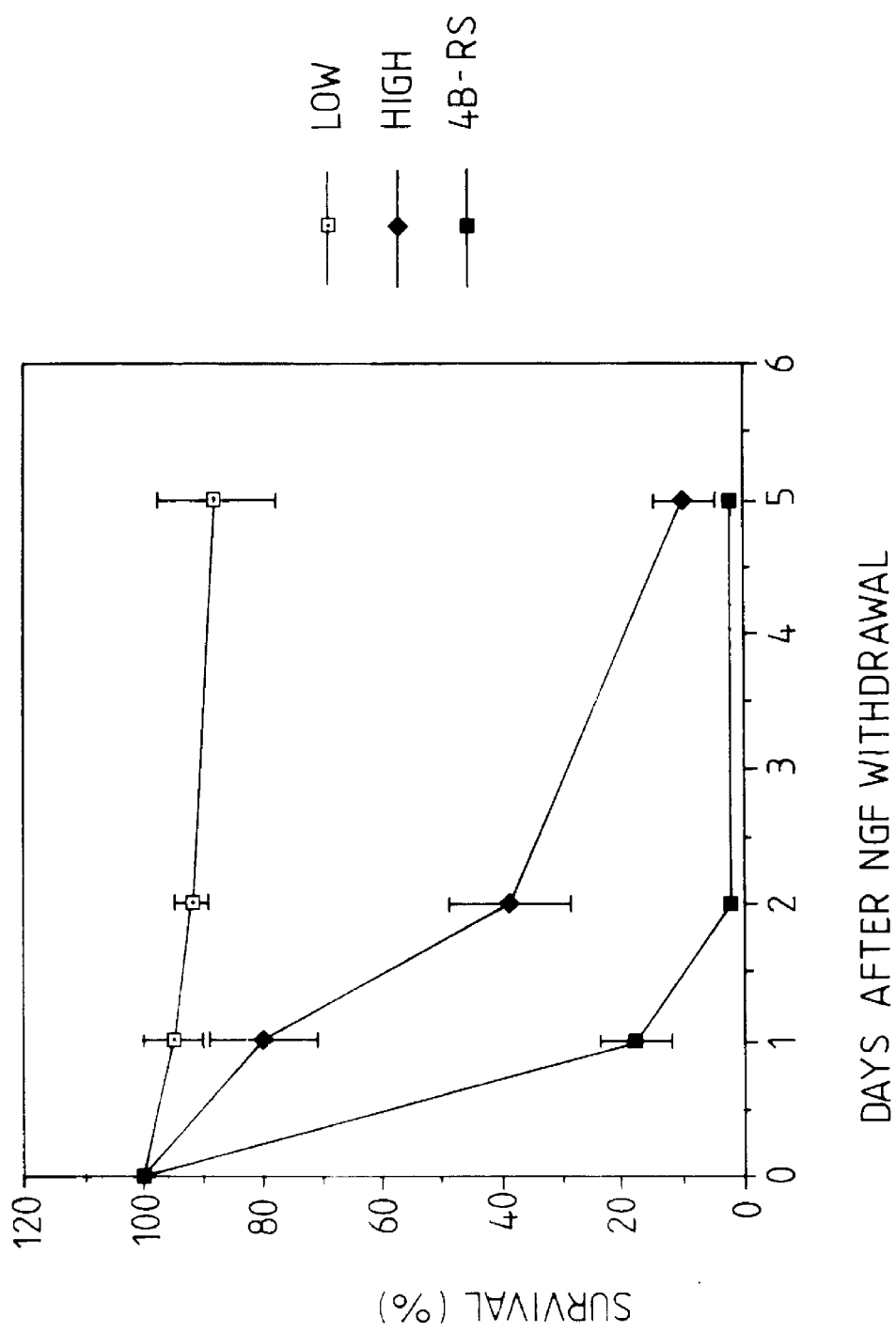

FIG. 9 is a graphical representation of the rate of death in vitro after NGF withdrawal of PC-12 cells having different levels of $p75^{NGFR}$ expression.

Figure 10:
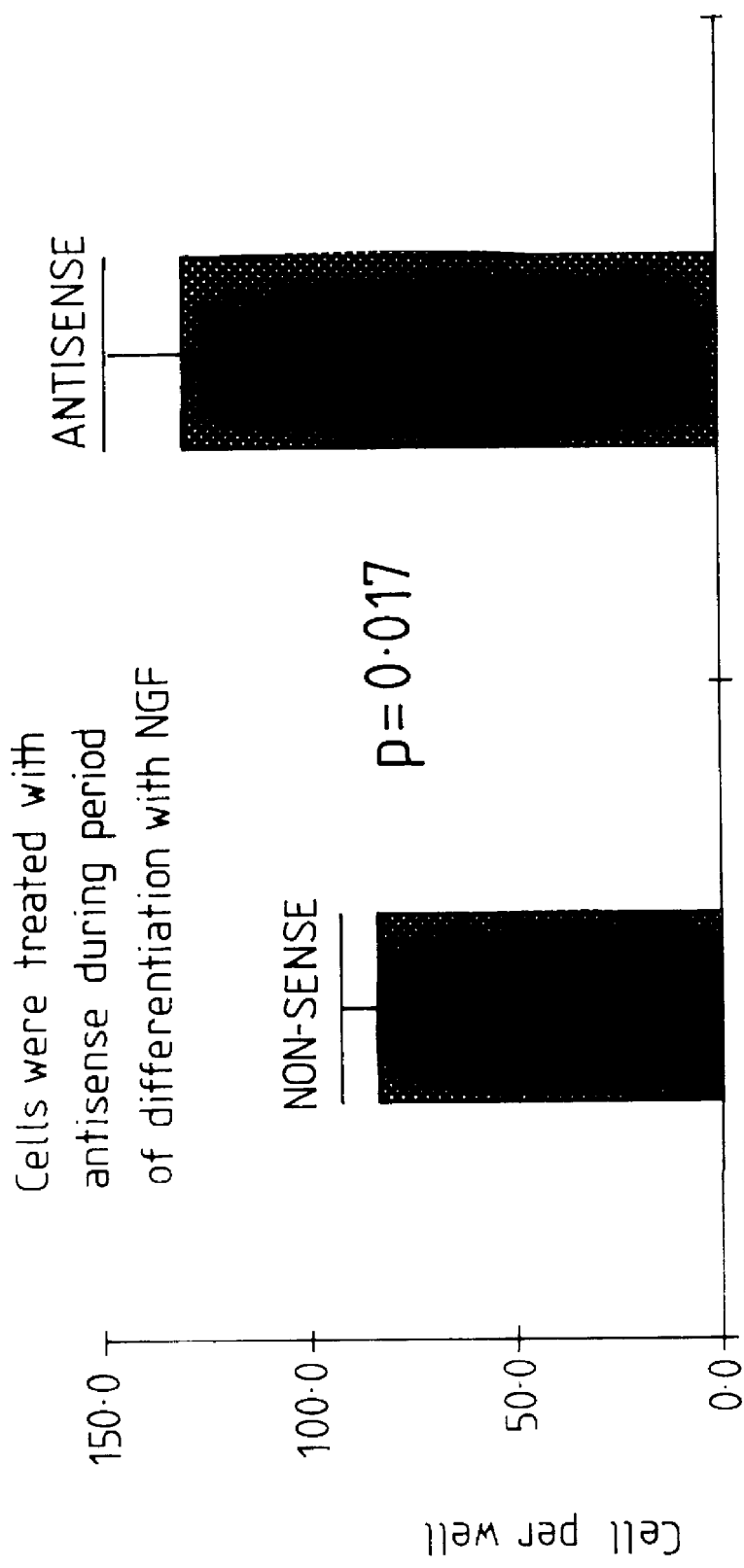

FIG. 10 is a graphical representation of survival in vitro after NGF withdrawal of PC-12 cells treated with $p75^{NGFR}$ antisense (SEQ ID NO:1) (5 μM) or non-sense (SEQ ID NO:9) (5 μM).

EXAMPLE 1

Preparation of Oligonucleotides

Sense and antisense oligonucleotides were prepared by standard synthesis procedures. Where necessary, oligonucleotides were purified in HPLC, eluted in acetonitrile, lyophilised and reconstituted in $H_2O$ to remove volatile contaminants and then further purified by Sephadox G25 gel-filtration prior to usage. Preferred oligonucleotides are phosphorothioate oligonucleotides.

EXAMPLE 2

Down Regulation of $p75^{NGFR}$ Receptor Expression

Figure 1A:
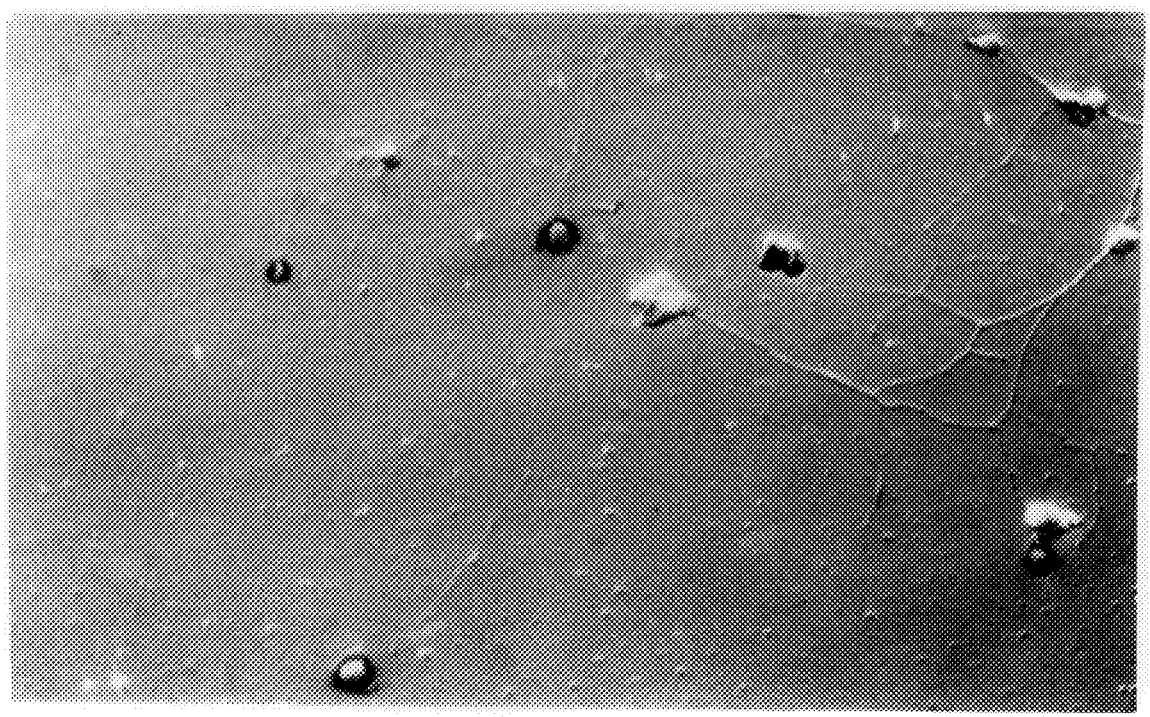
FIG. 1A is a photographic representation following autoradiography of P2 mouse DRG cells treated with $^{35}S$ 5'-labelled antisense oligonucleotides.

The expression of $p75^{NGFR}$ receptor in sensory neurones from DRG was down regulated at various stages of development by using $p75^{NGFR}$ antisense phosphorothioate oligonucleotides. Phosphorothioates were chosen for their resistance to nucleases which confers exceptionally high stability both in vitro and in vivo (3). To facilitate penetration of oligonucleotides into cells, cells were triturated in the presence of oligonucleotides following formation of a single-cell suspension and prior to plating out. Autoradiographic analysis indicated that oligonucleotides entered at least 65% of neurones. FIG. 1A shows the results of autoradiography of P2 mouse DRG cells treated with 35S 5'-labelled antisense oligonucleotides. The label was incorporated into the oligonucleotides using T4 polynucleotide kinase. Cultures were incubated with oligonucleotides for 2 days, dipped in emulsion and exposed for 7 days. The majority of neurones took up labelled oligonucleotides, whereas few of the glial cells did so. The "halo" effect around labelled cells reflects thinning of the emulsion over the large, rounded neurones.

The effectiveness of the $p75^{NGFR}$ antisense was assessed by immunostaining cultures of sensory neurones from 2 day old (P2) rats with an anti-$p75^{NGFR}$ antibody, 2 days after treatment with either antisense, sense, or non-specific oligonucleotides.

Figure 1B:
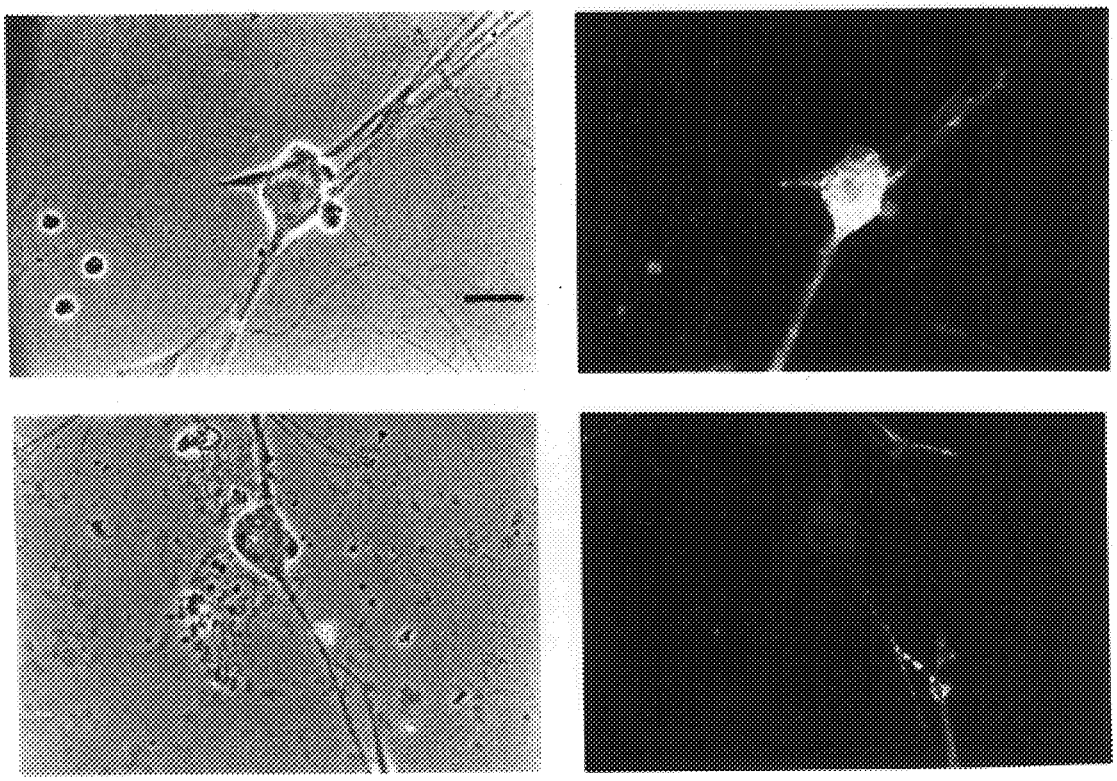
FIG. 1B is a photographic representation of phase-contrast and immunofluorescence photographs of cells from a control (sense oligonucleotide treated) culture (top panels) and an antisense treated culture (bottom panels).

The results are shown in FIG. 1B which provide corresponding phase-contrast and immunofluorescence photographs of cells from a control (sense oligonucleotide treated) culture (top panels) and an antisense treated culture (bottom panels). Whereas the control culture showed strong $p75^{NGFR}$ expression on both the cell body and process, expression in the antisense treated cell and its process was negligible. The streaky staining surrounding the neuron in the antisense culture represents $p75^{NGFR}$ expression in glial cells, which showed less down regulation than in neurones. Although the majority of survival assays were performed in mouse cells, rat cells (preparations of which contained a high proportion of glial cells, unlike mouse preparations) were used here as the monoclonal antibody does not detect mouse $p75^{NGFR}$. Single-cell suspensions of P2 rat DRG cells were prepared as previously described (4) and triturated for one minute in a Gilson micro pipette in the presence of oligonucleotides, plated onto fibronectin-coated plastic slides and incubated for two days in the presence of NGF 1 ng/ml. They were then washed prior to incubation with a monoclonal antibody to $p75^{NGFR}$ (MC192, Boehringer, Germany) and a fluoroscein isothiocyanate (FITC) conjugated sheep anti-mouse antibody (Silenus, Australia). Cells were then washed prior to fixation in 4% v/v paraformaldehyde. The bar represents 25 μm. The results show that following antisense treatment, a large number of neurones had very low levels of receptor expression (FIG. 1B).

Figure 1C:
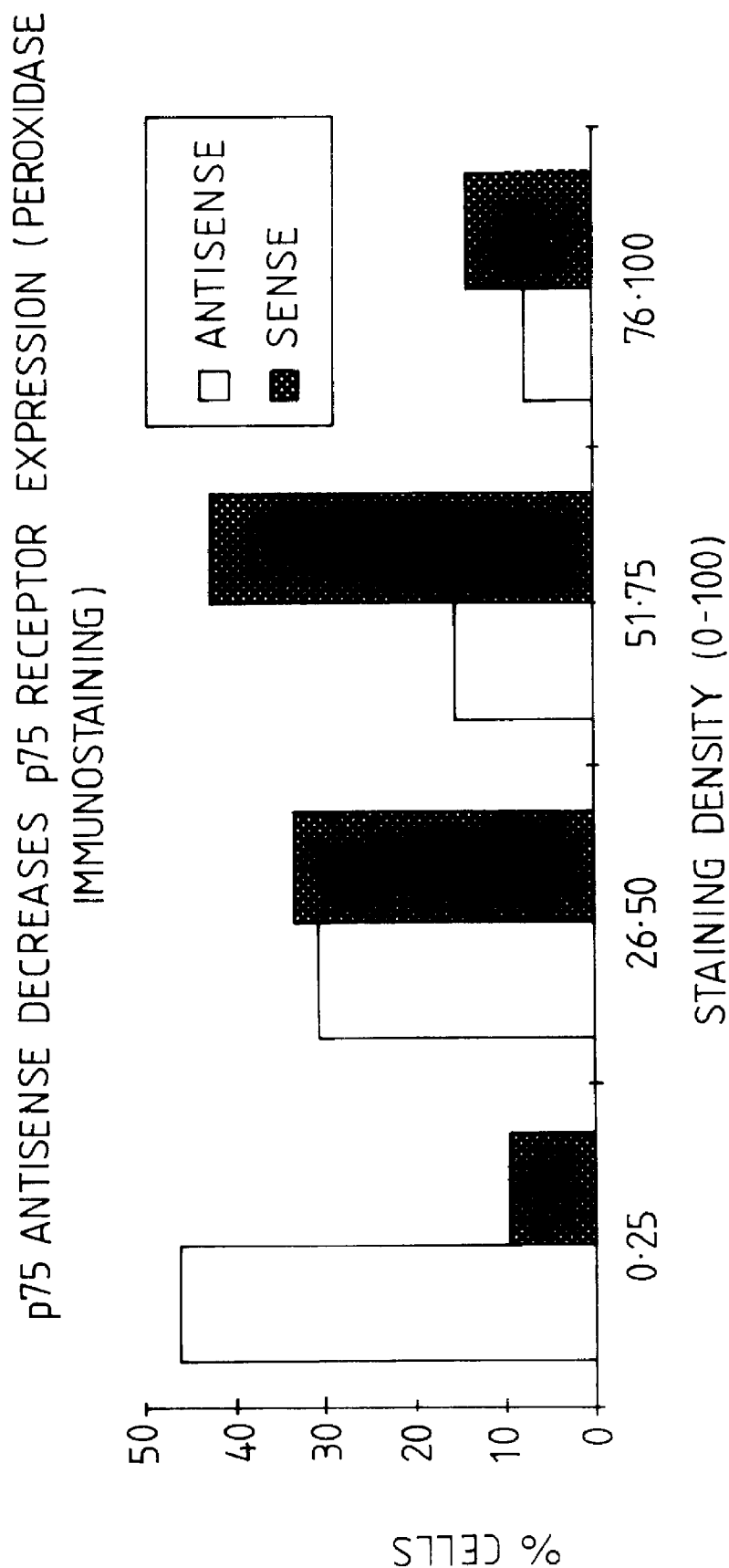
FIG. 1C is a graphical representation showing frequency distribution of $p75^{NGFR}$ immunostaining in sense and antisense treated P2 rat sensory neurones after 2 days in culture.

Quantitative analysis of the levels of expression was then conducted. The analysis was performed on 40 cells from each category. Staining was performed using the MC192 monoclonal antibody and a biotinylated sheep anti-mouse antibody (Vector Laboratories, USA) and a peroxidase staining kit (Vectastain Elite kit, Vector Laboratories, USA) after paraformadehyde fixation. Staining intensity was quantified using a computerised image-analysis system (Leading Edge, Australia), expressed on an arbitrary linear scale of zero to 100 and cells divided into one of four categories along this scale. Cells in the lowest category (0–25) had staining virtually indistinguishable from background, and the proportion of these increased from 9% in control cultures to 48% in antisense cultures. The results are shown in FIG. 1C and reveal a significant reduction in expression of $p75^{NGFR}$ receptor in a proportion of antisense treated neurones when compared with sense controls.

The number of neurones expressing background levels of $p75^{NGFR}$, increased from <10% in sense treated cultures to >45% in the antisense treated cultures. A more sensitive analysis using smaller density subdivisions than in FIG. 1C would detect lesser degrees of down regulation and thus yield a higher percentage of cells down regulating $p75^{NGFR}$.

EXAMPLE 3

Effect on Survival of Sensory Neurones Following Antisense Treatment

Figure 2:
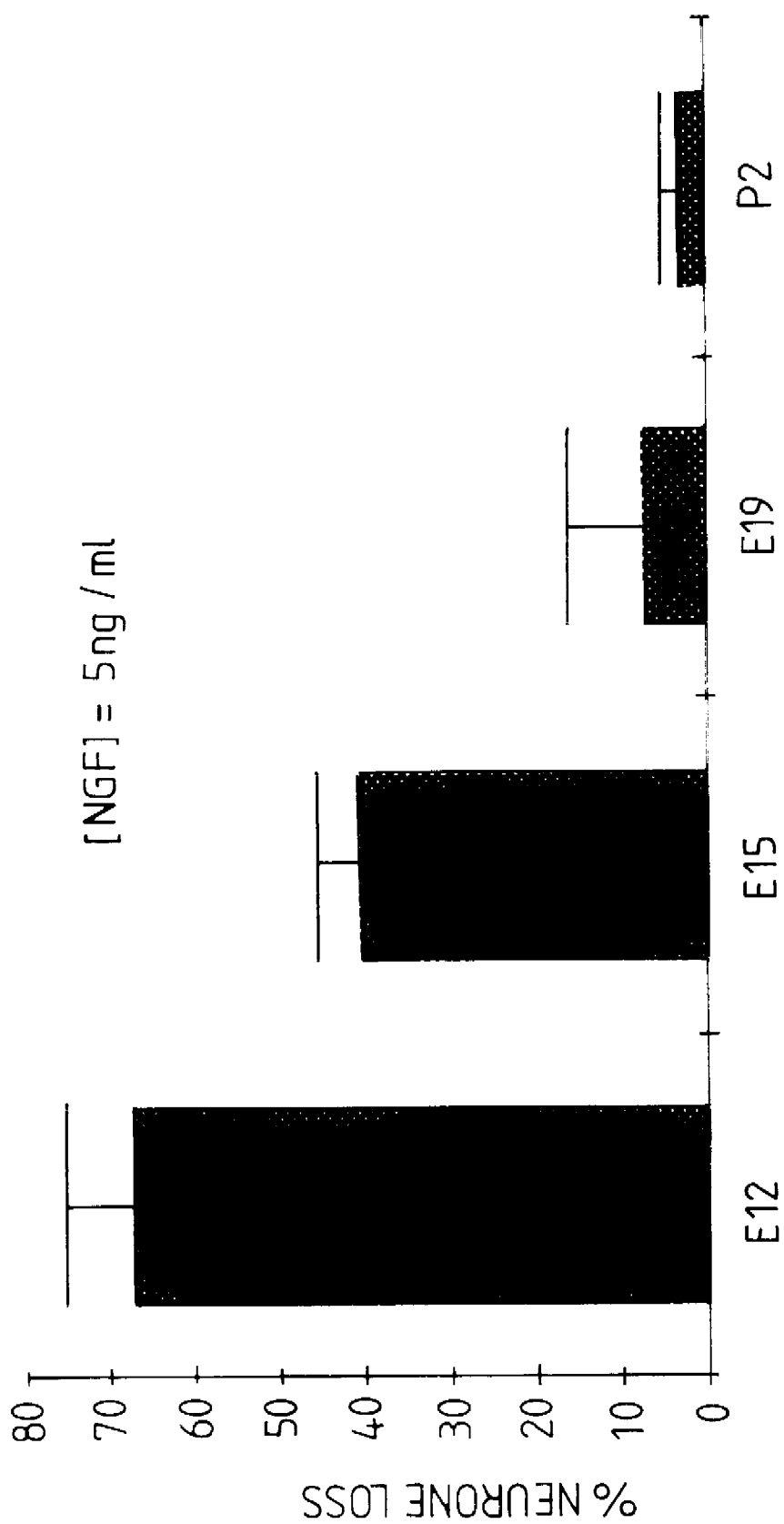
FIG. 2 is a graphical representation of DRG neuronal loss after 2 days in culture in the presence of NGF and the $p75^{NGFR}$ antisense oligonucleotide expressed relative to the number of neurones which survived in the presence of the corresponding sense oligonucleotide.

The efficacy of the antisense treatment was established in Example 2. The effect on the survival of sensory neurones derived from mice ranging in age from E12 to P2 was then determined. FIG. 2 shows DRG neuronal loss after 2 days in culture in the presence of NGF (Boehringer, Germany) and the p75$^{NGFR}$ antisense oligonucleotide (RAT AS, shown in Table 1 legend) expressed relative to the number of neurones which survived in the presence of the corresponding sense oligonucleotide. It can be seen that antisense treatment decreased the NGF-dependent survival at E12 and E15, but not significantly at E19 or P2. Single cells were prepared and treated with the appropriate oligonucleotide as for FIG. 1B and plated at low cell density (approximately 50 cells per well for E15-P2, 300 for E12) in Terasaki plates in Monomed (CSL, Australia) plus 10% v/v FBS. Cell counts were determined at the start and end of the experiments, and neuronal survival, as judged by phase-microscopic criteria of neuronal morphology, phase-brightness, cytoplasmic integrity and non-granularity, was determined. To establish veracity of the counting procedure, counts were initially performed "blind" by 2 experienced cell counters, in almost all cases with close agreement in results. This comparison of counts by different observers was repeated periodically to ensure that accuracy was maintained. Bars and error bars represent means and standard errors for 6 or more individual assays. Oligonucleotide concentration was 10 $\mu$M at E12 and 5 $\mu$M at all other stages (10 $\mu$M was found to be optimal at E12).

It was found that in the presence of a high concentration (e.g.>5 ng/ml) of exogenously added NGF, the survival of E12 and E15 sensory neurones was markedly diminished by treatment with antisense oligonucleotides when compared to neurones treated with sense (or non-sense) 18-mer oligonucleotides (FIG. 2). However, there was no significant decrease in survival of E19 and P2 sensory neurones following antisense treatment (FIG. 2), although DRG neurones have been shown to remain highly NGF-dependent until at least P2 (4,5). This finding demonstrated that sensory neurones at the stage of target field innervation require p75$^{NGFR}$ for NFG-mediated survival, whereas sensory neurones at later developmental stages seem unaffected although, as shown above, antisense treatment significantly reduced p75$^{NGFR}$ expression at P2. These results also showed that the relative abundance of p75$^{NGFR}$ molecules on P2 neurones was not required for NGF-mediated survival suggesting that this receptor may play another role in cell function.

EXAMPLE 4

To further investigate the role of p75$^{NGFR}$ neurones treated with antisense were cultured in the absence of added NGF. As expected, this resulted in the rapid death of E12 and E15 neurones. Surprisingly, however, the P2 sensory neurones showed a marked increase (>50%) in their survival compared to sense controls (FIG. 3 & Table 1). The apoptotic nature of DRG cell death at P2 was confirmed by the ability of cycloheximide to prevent death in non NGF treated cells (FIG. 3). A dose-response analysis established that antisense mediated survival was optimal at an antisense concentration of 5 $\mu$M. (Survival was 19±4% without antisense, 29±3% at 0.5 $\mu$M, 47±5% at 2 $\mu$M, 50±5% at 5 $\mu$M and 31±6% at 10 $\mu$M antisense). This effect was excluded in the present analysis by using sense and antisense treated cutures as controls rather than non oligo treated controls. Increased survival was observed in all seven antisense experiments involving sensory neurones from P2 mice, and similar effects were seen in sensory neurones from rats and chicken taken at the comparable development stage (Table 1). Further, species sequence specificity was observed in that the chick antisense had no effect on rat cells but had a dramatic effect on chick cells. Both chick and rat antisense oligos enhanced survival in mouse, although the effect was more marked with the rat sequence. Thus, in a number of species, down regulation of p75$^{NGFR}$ increased cell survival, implying that this receptor promotes cell death at a specific stage of development. Immunostaining confirmed that surviving cells in antisense cultures showed marked down regulation of p75$^{NGFR}$.

To eliminate the possibility that this effect was due to the presence of an unidentified ligand in serum, the experiment was repeated in the absence of serum. The increment in survival due to antisense was undiminished in the absence of serum. Furthermore, the survival effect was apparently independent of glial cell contamination, as glial contamination was negligible in the absence of serum. Even in the presence of serum, the survival effect occurred in both rat cultures (significant glial contamination) and mouse cultures (glial contamination less than 10%). The ability of antisense to promote survival without serum and regardless of degree of glial contamination argues against the interpretation that there is another ligand or that p75$^{NGFR}$ downregulation promotes survival by allowing a greater proportion of hypothetical trace amounts of NGF in the cultures to bind to trkA. The latter possibility was definitively excluded by showing that addition of anti-NGF antibody did not decrease the antisense-induced survival effect (Table 1).

EXAMPLE 5

Analysis of Switch in p75$^{NGFR}$ Function

The approximate stage at which the switch in p75$^{NGFR}$ function occurs was elucidated by experiments carried out on E19 mouse sensory neurones. In this case treatment with antisense, in the absence of NGF, did not enhance their survival (Table 1). However, if cultured initially in the presence of low concentrations of NGF (1 ng/ml), to promote their short term survival, the antisense treated neurones subsequently behaved in a similar manner to P2 neurones and showed a significant increase in survival when compared to sense controls, which became more evident with time in culture (FIG. 4). These results demonstrate that a fundamental change in p75$^{NGFR}$ function occurs at around E19: from mediating neuron survival to initating cell death. The ability to promote cell death at P2 was only observed in the absence of a high concentration of exogenously added NGF.

EXAMPLE 6

The p75$^{NGFR}$ receptor is important in transducing the survival effect of NGF during the phase of neuronal target selection (approximately E13 to E17). As trkA is highly expressed during this period (7), this result is consistent with the hypothesis that the high-affinity NGF receptor required both p75$^{NGFR}$ and trkA. The role of P75$^{NGFR}$ in mediating the NGF response at this time is unlikely to be due to its postulated localising or recruiting role (9), as the cells in these experiments were bathed in a high concentration of NGF, and a localising role would be superfluous. In the early postnatal period, p75$^{NGFR}$ was shown to have an opposite role, that of promoting cell death, but only in the absence of high levels of NGF. The reversal of the role of p75$^{NGFR}$ coincides with the down regulation of trkA mRNA in P2 DRG to levels undetectable by PCR (FIG. 4B). One hypothesis to explain these findings is that, in the presence of trkA, p75$^{NGFR}$ interacts with it to form a high-affinity complex capable of transducing the NGF survival signal, but that in the absence of trkA acts as a constitutive death signal. Thus, $p75^{NGFR}$ may mediate a signal for programmed cell death, but only when NGF is absent or at a low concentration. In in vitro experiments, "high levels" of NGF means greater than endogenous levels such as >3–5 ng/ml and preferably >20 ng/ml. A "lower level" is regarded as normal endogenous levels. The presence of NGF can prevent $p75^{NGFR}$ from inducing apoptosis. This would also explain the NGF-dependency of P2 DRG neurones despite the absence of trkA. The mechanisms by which $p75^{NGFR}$ may initiate apoptosis, and NGF prevents this process, are unclear.

EXAMPLE 7

In Vivo Model

Post natal day 4 (P4) Wistar rat pups of either sex provide a convenient in vivo model for testing the oligonucleotides of the present invention. The pups were operated on under ice-induced anesthesia. The left sciatic brachial nerves of each pup were exposed and axotomised using a pair of iridectomy scissors. The proximal stump of the sciatic nerve was wrapped with a 1-mm³piece of pluronic gel (eg 20%) soaked gel foam (Upjohn) containing sense or antisense oligonucleotides or PBS. The contralateral sciatic nerve and DRG served as the intact control side. A 5-0 Ethicon silk suture was used to close the skin incision. The pups were then warmed until they were fully conscious and they were then reunited with their mothers. The effectiveness of the sciatic nerve axotomy was apparent by the post-surgical ataxia of the hindlimb and the completeness of the nerve transection verified by postmortem dissection.

After 5 days, the animals were deeply anesthetised and then perfused transcardially with 4% v/v paraformaldehyde and 0.5% w/v glutaraldehyde in 0.1 M sodium phosphate buffer at pH 7.3. Immediately after perfusion the vertebrae overlying the lumbar DRGs were removed and the whole animal was immersed in the same fixative overnight. The following day, the left (axotomised) and right (intact) L5 or C8 DRGs were removed and postfixed for a further 24 hr. These DRGs were then dehydrated and embedded in paraffin. Serial sections 8 μm thick were cut and mounted on gelatinised slides and stained in 0.1% w/v cresyl violet.

Neurons displaying a prominent nucleolus were counted at a final magnification of 400× through a graticule placed in the eye-piece of a Leitz microscope. Counts were performed on every fifth or tenth section. The raw counts were corrected for multiple nucleoli and then for split nucleoli using Abercrombie's formula. Mean nucleolar diameter measurements showed that axotomised neurons did not have shrunken nucleoli. The proportion of neurons lost was calculated as a percentage as follows:

$$\frac{[\text{neurons in the intact } L5 \ DRG] - [\text{neurons in the axotomised } L5 \ DRG]}{\text{neurons in the intact } L5 \ DRG} \times 100$$

To ensure an accurate estimate of neuronal loss, two steps were taken. First, the section thickness exceeded the greatest nucleolar height by a factor of about 4. This factor is well above the critical factor of 1.5 which is needed to ensure that the Abercrombie correction factor is reliable and not seriously biased (10). Secondly, contralateral controls were used throughout and all comparisons between animals were based on proportional rather than absolute values. Where proportional values are used, Abercrombie's correction factor is not necessary, since any biases introduced in the counting should be common to both sides and cancel out when the ratio is calculated.

The means and standard errors of means (SE) were calculated for each group and statistical differences between groups were determined by using the Student's t test.

EXAMPLE 8

Neuronal Survival In Vitro in the Presence of $p75^{NGFR}$ Antisense Oligonucleotides P2 mouse DRG neurones were prepared and cultured as described above and survival assessed after 4 days in the presence of a high concentration (about 50 ng/ml) NGF (without oligonucleotides) or either of two different $p75^{NGFR}$ antisense oligonucleotides (without NGF). The oligonucleotides were 5'-ACCTGCCCTCCTCATTGCA-3' (SEQ ID NO. 1), referred to as "5-AS" in FIG. 6; and 5'-AGTGGACTCGCGCATAG-3' (SEQ ID NO. 4) referred to as "3-AS" in FIG. 6.

A control non-sense oligonucleotide (scrambled antisense oligonucleotide) was also used with the sequence 5'-CTCCCACTCGTCATTCGAC-3' (SEQ ID NO. 9). Survival was enhanced by application of either NGF or $p75^{NGFR}$ antisense oligonucleotides whereas application of a random sequence control oligonucleotide did not increase survival compared to the "no-oligo" group (FIG. 6).

A 26-mer antisense sequence to rat $p75^{NGFR}$ based on the 5' regions (5' CATTGCACGCCTCCGGCGTCAGCGCT-3' SEQ ID NO:8) was tried in separate experiments and found to be effective but less so than the 18-mer described above.

Most of the oligos used were obtained from more than one synthesis over the duration of the experiments, and in each case the effect of the oligos was consistent over separate syntheses. Oligos were purified by reverse-phase HPLC, eluted in acetonitrile, lyophilized and reconstituted in $H_2O$ twice to remove volatile contaminants, then further purified by Sephadex G25 gel-filtration prior to usage.

\* $p<0.05$, Student's T-test.

\*\* $p<0.05$ for each of 7 experiments.

EXAMPLE 9

Construction of Neuronal Cell Lines Expressing Defined Amounts of $p75^{NGFR}$ The following cell lines were created:
1) PC12-2CL: This line has very low $p75^{NGFR}$ expression and accordingly does not die when NGF is withdrawn.
2) PC12-2CH: Moderate level of $p75^{NGFR}$ expression, and fairly rapid death when NGF is withdrawn.
3) PC12-4A & PC12-4B: High level of $p75^{NGFR}$ expression, and rapid death upon NGF withdrawal.
4) PC12-4BS: Very high level of $p75^{NGFR}$ expression, and very rapid death upon NGF withdrawal.
5) PC12-4BRS: Highest level of $p75^{NGFR}$ expression, and extremely rapid death upon NGF withdrawal.
1) PC12-4BRS: Very high $p75^{NGFR}$ expression.

PC12 cells were stably transfected with a $p75^{NGFR}$ expression construct by electroporation. Cells were co-electroporated with the "geo" cDNA (which combines neomycin resistance gene with the gene for beta-galactosidase). Colonies were obtained in the presence of geneticin and expanded clonally to obtain new cell lines which were then characterized. Initially, cells were stained for p75$^{NGFR}$ using immunoperoxidase after fixation, and on this basis two lines were chosen for further development. These were then subjected to FACS sorting and amplification, and the top 15% p75$^{NGFR}$ expressing cells were retained to obtain high-expressing line (PC12-4AS and PC12-4BS). Some cells were retained, expanded in culture and the FACS sorting process was repeated three times to obtain a PC12 variant expressing p75$^{NGFR}$ at a very high level (PC12-4BRS). In each round of FACS sorting, only the top 15% p75$^{NGFR}$ expressing cells were retained. Throughout, it was necessary to maintain the cells in high serum and in the absence of NGF, to prevent development of a neuronal phenotype.

After each sort, cells in the top 15% p75$^{NGFR}$ expression bracket were frozen down in aliquots.

PC12-4AS, PC12-4BS and PC12-4ARS cells were thawed, grown in culture and shown by immuno-peroxidase staining to retain a high level of p75$^{NGFR}$ expression.

PC12-2C high and low expressing cells were obtained from control transfected PC12 cells, i.e. cells transfected with the geo gene but not with p75$^{NGFR}$. They therefore expressed only the endogenous p75$^{NGFR}$ gene. These were subjected to sorting, and the 15% of cells with the highest expression were collected and both used immediately for experiments and frozen down in aliquots. These cells were named PC12-2CH. Similarly, the 15% of cells with the lowest level of expression were collected and both used immediately for experiments and frozen down in aliquots. These cells were named PC12-2CL. Northern blot analysis confirmed the levels of p75$^{NGFR}$ expression in each line. In descending order of p75$^{NGFR}$ expression: PC12-4BRS, PC12-4B, PC12-2CH, PC12-2CL.

EXAMPLE 10 p75$^{NGFR}$ Induced Cell Death and Rescue by p75$^{NGFR}$ Antisense Downregulation PC12 cells can be induced to differentiate into neurones by withdrawal of serum and addition of NGF. They then become dependent on NGF, and die after NGF deprivation.

To analyse further the role of p75$^{NGFR}$, the neuronal cell-lines described in Example 9 were analysed. These cell-lines were designed to express defined amounts of p75$^{NGFR}$, but to be identical in all other aspects.

An NGF withdrawal experiment was performed, using three of these cell-lines:

| | |
|---|---|
| PC12-4BRS | (highest p75$^{NGFR}$ expression) |
| PC12-2CH | (high p75$^{NGFR}$ expression) |
| PC12-2C1 | (low p75$^{NGFR}$ expression) |

After withdrawal of NGF, the cells with low p75$^{NGFR}$ survived, whilst those with higher levels died. Further, the rate of death increased with increasing p75$^{NGFR}$ expression (FIG. 7). From the time of NGF withdrawal (when cell death begins), anti-NGF antibody was added thereby excluding the interpretation that p75$^{NGFR}$ acted as an NGF "sponge".

These results show that p75$^{NGFR}$ induces neuronal death in a cell line which normally expresses both p75$^{NGFR}$ and trkA. Moreover, it is the excess of p75$^{NGFR}$ that is crucial in inducing death. When in excess, p75 $^{NGFR}$ induced death, and the rate of death depended on the amount of p75$^{NGFR}$.

An antisense experiment was also performed. p75$^{NGFR}$ antisense oligonucleotide treatment increases survival of PC12 neurones (which express normal levels of p75$^{NGFR}$) in the absence of NGF (FIG. 8).

EXAMPLE 11

In vivo Models to Test Antisense Oligonucleotides

The following nerve injury in vivo models may be used to test the antisense oligonucleotide of the present invention.

1) Peripheral nerve transection injury and peripheral nerve crush injury These lesions induces sensory and motor neurone death. Both of these lesions are performed in sciatic and brachial nerves, and neuronal counts undertaken in L5 and C8 level spinal neurones respectively. The importance of these lesion models is that the affected neurones express p75$^{NGFR}$ and are NGF-sensitive.

2) Fimbrio-fornix lesion

This is performed by stereotatic ablation, requiring specialised equipment and expertise. It is considered to be the best animal model for investigating Alzheimer's disease in rats: the fimbrio-fornix lesion induces death of the cholinergic forebrain neurones, which are the principal p75$^{NGFR}$-expressing neurones in the brain and which are the primary focus of Alzheimer's disease.

EXAMPLE 12

Neuronal Uptake and Transport of Antisense Oligonucleotides

Biotinylated antisense p75$^{NGFR}$ oligonucleotides were shown to be retrogradely transported by axotomised sensory neurones. Sensory neurones in the lumbar dorsal root ganglia normally do not stain for biotin. However, after the injection of biotin-labelled antisense p75$^{NGFR}$ oligonucleotides into the proximal stump of the sciatic nerve many neurones are biotin positive (FIG. 7). In these experiments, biotinylated oligonucleotides were injected into the proximal stump of the transected sciatic nerve of neonatal rats and the stump was tied off. The injections were made using a glass micropipette with tip diameters ranging from 50–100 mm and the contents expelled by pneumatic means using a picospritzer. After 7 days, the animals were perfused rapidly with 2% paraformaldehyde, the ipsilateral and contralateral L4 and L5 dorsal root ganglia removed. The ganglia were placed in Tissue-Tek and frozen in nitrogen cooled isopentane. Sections 10 mm thick were cut and mounted on AES coated slides and stained using the avidin-biotin-peroxidase complex (Vectstain Elite kit, Vector Laboratories).

EXAMPLE 13

Down Regulation of p75$^{NGFR}$ in vivo by Antisense Oligonucleotides

Treatment with antisense p75$^{NGFR}$ oligonucleotides reduced the expression of p75$^{NGFR}$ protein in axotomised sensory neurons in the lumbar dorsal root ganglia. In intact dorsal root ganglia (not treated with antisense oligonucleotides), there were a large number of p75$^{NGFR}$-positive neurones (FIG. 8A) whereas in the axotomised dorsal root ganglia treated with p75$^{NGFR}$ antisense oligonucleotides there was a marked reduction in the number of p75$^{NGFR}$ positive cells. The low-affinity NGF receptor was visualised using the monoclonal antibody MC 192 (Boehringer Mannheim) after fixation of tissue in paraformaldehyde and methanol.

The effect of p75$^{NGFR}$ antisense oligonucleotides on expression of p75$^{NGFR}$ was quantified by counting dorsal root ganglia cells positive for p75$^{NGFR}$ after being treated with PBS, sense and antisense oligonucleotides. Percentages of p75$^{NGFR}$ positive neurones in lumbar dorsal root ganglia are shown in FIG. 8B. In the PBS and sense control groups approximately 64% of sensory neurones are p75$^{NGFR}$ positive. However, a dramatic reduction in the number of p75$^{NGFR}$ positive cells is seen in animals treated with antisense p75$^{NGFR}$ oligonucleotides. Total number of neurones counted per group were: 224 (PBS), 233 (sense), 163 (antisense).

EXAMPLE 14

Prevention of in vivo loss of axotomised sensory neurones was demonstrated following treatment with p75$^{NGFR}$ antisense oligonucleotides (FIG. 5). Brachial (median or ulnar nerves) or the sciatic nerve were transected in 3 day-old rats and treated with small pieces of gelfoam, approximately 1 mm$^3$, which were soaked in 20% pluronic gel solution (BASF) containing PBS or 50 μM oligonucleotide.

FIG. 5 summarises the extent of loss of axotomised sensory neurones in cervical (C8) and lumbar (L5) dorsal root ganglia. In the sense, and PBS, treated control animals, the loss was about 40%. However, treatment with antisense oligonucleotides dramatically reduced the loss, in both ganglia, to about 15% which represents a rescue of 70% of neurones which would have otherwise have died.

Oligonucleotides used were as follows: Rat 3' AS (SEQ ID NO:4) and Rat 3' Sense (SEQ ID NO:5).

After 5 days, the animals were transcardially perfused with 2% paraformaldehyde, the cervical (C8) and lumbar (L5) DRG dissected out and neuronal counts were performed as described in Example 7. Statistical differences between groups was estimated using Student's t-test.

TABLE 1

| SPECIES | AGE | CELLS PLATED (mean per well) | N (no. of wells) | INCREASE IN SURVIVAL |
|---|---|---|---|---|
| MOUSE (NO SERUM) | P2 | 22 | 24 | 57% (CHICK AS) 126%* (RAT AS) |
| MOUSE | P2 | 50 | 7 × 6 | 58%** |
| MOUSE | E19 | 56 | 6 | 14% |
| MOUSE | E15 | 65 | 6 | -5% |
| MOUSE | E12 | 300 | 6 | 0% |
| RAT | P2 | 51 | 6 | 41%* |
| CHICK | E11 | 42 | 6 | 105%* |

LEGEND TO TABLE 1

Enhancement of survival of antisense treated DRG neurones after 48–60 hours in the absence of NGF. Experiments were performed in the present of 10% FBS unless otherwise indicated. Viable cells were counted after plating and at 48–60 hours in individual Terasaki wells for each of the antisense and control cultures. Results are expressed as the increase in survival with antisense compared to control cultures (containing either sense or non-sense oligonucleotides: numerous experiments established that there was no difference in survival between the sense (SEQ ID NO:5) and non-sense (SEQ ID NO:7) (random sequence) cultures), to rule out the additional variations seen between survival in non oligo treated and control oligo treated cultures. Representative absolute survival figures, from one of the P2 mouse DRG experiments with serum, were 21.6% (untreated), 28.9% (non-sense), 51% (antisense), 48% (NGF 5 ng/ml, no oligo) and 64% (NGF 50 ng/ml). Antisense oligonucleotides (5 μM) to rat p75$^{BGFR}$ mRNA (RAT AS (SEQ ID NO:4)) increased P2 mouse neuronal survival by an average 58% in 7 experiments, although increases of approximately 100% were seen in some experiments. An anti-NGF monoclonal antibody (Boehringer, Germany) was added in 4 of the P2 experiments and was found not to diminish this effect. An increase in survival also occurred in mouse cultures using the chick antisense sequence (CHICK AS (SEQ ID NO:6)) although to a lesser extent than with the RAT AS. In P2 rat neurones, only RAT AS caused an increase in survival, whereas CHICK AS was able to increase survival in cultures of E11 chick DRG neurones (developmentally close to the P2 stage in the rat). The survival-enhancing effect of p75$^{NGFR}$ antisense treatment was not apparent in mouse DRG at E12, E15 or E19. 18-mer phosphorothioate oligonucleotides were used in all cases, and the sequences chosen were directed against the 3' end of the coding region.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES:

1. Levi-Montalcini, R. *Ann. Rev. Neurosci* 5: 341–362, 1982.
2. Lee, K. F. et al., *Cell* 69: 737–749, 1992.
3. Agrawal, S. et al., *Proc. Natl. Acad. Sci. USA* 88: 7595–7599, 1991.
4. Murphy, M. et al., *Neurosci* 117: 1173–1182, 1993.
5. Yip, H. K. et al., *Neurosci* 4: 2986–2992, 1984.
6. Meakin, S. O. et al., *Proc. Natl. Acad. Sci. USA* 89: 2374–2378, 1992.
7. Martin-Zanca, D. et al, *Genes Dev.* 4: 683–694, 1989.
8. Hempstead, B. L. et al., *Nature:* 350: 678–682, 1991.
9. Jing, S. et al., *Neuron* 9: 1067–1079, 1992.
10. Clarke, P.G.H., *Trends Neurosci* 15: 211–212, 1992.
11. Pollin, M. M. et al., *Development* 112: 83–89, 1991.
12. Klein et al., *Cell* 65: 189, 1991.
13. Svinarchuk et al., *Biochemie* 75: 49-54, 1993.
14. Ortigao et al., *Biochemie* 75: 29–34, 1993.
15. Degols et al, *Antisense Res Dev* 2: 293–301, 1992.
16. Bunnell et al., *Somat Cell Mol Genet* 18: 559–569, 1992.
17. Maniatis et al., *Molecular Cloning; A Laboratory Manual.* Cold Spring Harbor Laboratory, Cold Spring Harbor, N.Y., USA. 1982.

I claim:

1. A method of down regulating expression of the low affinity nerve growth factor (NGF) receptor, p75$^{NGFR}$ on a neurone, which comprises contacting said neurone with an effective amount of an antisense oligonucleotide to a portion of the gene encoding p75$^{NGFR}$, wherein said antisense oligonucleotide is about 17 to 26 nucleotides in length and comprises SEQ ID NO:1 or SEQ ID NO:4.

2. A method according to claim 1 wherein the antisense oligonucleotide is SEQ ID NO:1 or SEQ ID NO:4.

3. A method according to claim 1 or claim 2 wherein the antisense oligonucleotide is a phosphorothioate oligonucleotide or is conjugated to lipophilic groups, mesotetracarboxyporphine, poly-L-lysine or a protein via poly-L-lysine.

4. A method of facilitating neuronal survival in vitro or in vivo which comprises down regulating expression of p75$^{NGFR}$ on a neurone by contacting said neurone with an effective amount of an antisense oligonucleotide to a portion of the gene encoding p75$^{NGFR}$, wherein said antisense oligonucleotide is about 17 to 26 nucleotides in length and comprises SEQ ID NO:1 or SEQ ID NO:4, for a time and under conditions sufficient to reduce expression of p75$^{NGFR}$ such that neurone survival is facilitated.

5. A method according to claim 4 wherein the neurones are sensory neurones, sympathetic neurones, central cholinergic neurones, motor neurones or cerebellar neurones.

6. A method according to claim 5 wherein the neurones are sensory neurones.

7. A method according to claim 4 wherein the neurone is from a mammal.

8. A method according to claim 7 wherein the mammal is selected from the group consisting of human, livestock animal, laboratory test animal and captive wild animal.

9. A method according to any one of claims 4 to 8 wherein the antisense oligonucleotide is a phosphorothioate oligonucleotide or is conjugated to lipophilic groups, mesotetracarboxyporphine, poly-L-lysine or a protein via poly-L-lysine.

10. An oligonucleotide which down regulates expression of $p75^{NGFR}$ in neurones, said oligonucleotide having SEQ ID NO:1 or SEQ ID NO:4.

11. An oligonucleotide which down regulates expression of $p75^{NGFR}$ in neurones wherein said oligonucleotide is about 17–26 nucleotides in length and comprises SEQ ID NO:1 or SEQ ID NO:4.

12. An oligonucleotide according to claim 10 or 11 wherein the oligonucleotide is a phosphorothioate oligonucleotide or is conjugated to lipophilic groups, mesotetracarboxyporphine, poly-L-lysine or a protein via poly-L-lysine.

13. A pharmaceutical composition which down regulates expression of $p75^{NGF}$ in neurones comprising an oligonucleotide of at least one of SEQ ID NO:1 or SEQ ID NO:4 and one or more pharmaceutically acceptable carriers and/or diluents.

14. A pharmaceutical composition according to claim 13 wherein the oligonucleotide is a phosphorothioate oligonucleotide.

* * * * *

UNITED STATES PATENT AND TRADEMARK OFFICE
CERTIFICATE OF CORRECTION

PATENT NO. : 5,837,694
DATED : November 17, 1998
INVENTOR(S) : Graham L. Barret

It is certified that error appears in the above-identified patent and that said Letters Patent are hereby corrected as shown below:

On The Title Page, [54] TITLE: "NEURONE" should read --NEURON--

On The Title Page, [56] References Cited, U.S. PATENT DOCUMENTS: "of death" should read --or death--

Column 7, Line 27: "do" should read --dorsal--

Column 14, Line 7: "1) Peripheral nerve transection injury and peripheral nerve crush injury These lesions..." should read --1) Peripheral nerve transection injury and peripheral nerve crush injury These lesions...--

UNITED STATES PATENT AND TRADEMARK OFFICE
CERTIFICATE OF CORRECTION

PATENT NO. : 5,837,694
DATED : November 17, 1998
INVENTOR(S) : Graham L. Barret

It is certified that error appears in the above-identified patent and that said Letters Patent is hereby corrected as shown below:

Column 15, Line 39: "57%" should read --57%*--

Column 22, Line 10, Claim 13: "P75$^{NGF}$" should read --P75$^{NGFR}$--

Signed and Sealed this

Eighth Day of May, 2001

Attest:

NICHOLAS P. GODICI

Attesting Officer   Acting Director of the United States Patent and Trademark Office

SEQUENCE LISTING ( 1 ) GENERAL INFORMATION:

( i i i ) NUMBER OF SEQUENCES: 9

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:1:

ACCTGCCCTC CTCATTGCA          19

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:2:

TAGGCGGTCT GGTGACTTCG TTG          23

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:3:

ACATAGAGCT CCGTCAGGTT CCC          23

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:4:

AGTGGACTCG CTGCATAG          18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:5:

CTATGCAGCG AGTCCACT          18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:6:

GGTGGACTCG CTGTACAG 18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:7:

TCTTCTTCAA GCTTTGGC 18

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:8:

CATTGCACGC CTCCGGCGTC AGCGCT 26

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:9:

CTCCCACTCG TCATTCGAC 19